United States Patent [19]
Michel et al.

[11] Patent Number: 6,147,241
[45] Date of Patent: Nov. 14, 2000

[54] PROCESS FOR THE PREPARATION OF ORGANOSILICON-DISULFANES

[75] Inventors: Rudolf Michel, Freigericht; Jörg Münzenberg, Hanau, both of Germany; Carl Van Der Auwera, Temse, Belgium

[73] Assignee: Degussa-Hüls Aktiengesellschaft, Frankfurt am Main, Germany

[21] Appl. No.: 09/417,897

[22] Filed: Oct. 14, 1999

[30] Foreign Application Priority Data

Oct. 21, 1998 [DE] Germany .......................... 198 48 482

[51] Int. Cl.$^7$ ....................................................... C08F 7/08

[52] U.S. Cl. .............................................................. 556/427
[58] Field of Search ............................................. 556/427

[56] References Cited

U.S. PATENT DOCUMENTS 4,283,505  8/1981  Kleeberg et al. .................... 556/427 X
5,936,112  8/1999  Gobel et al. ............................ 556/427

*Primary Examiner*—Paul F. Shaver
*Attorney, Agent, or Firm*—Smith, Gambrell & Russell, LLP

[57] ABSTRACT

Organosilicon-disulfanes are prepared by decomposing organosilicon thiocyanates with an alkali metal alcoholate.

7 Claims, No Drawings

PROCESS FOR THE PREPARATION OF ORGANOSILICON-DISULFANES

INTRODUCTION AND BACKGROUND

The present invention relates to a process for the preparation of organosilicon-disulfanes.

Organosilicon-disulfanes are employed in the production of rubber articles containing silica as a filler. The use of organosilicon-disulfanes of high purity is of particular interest in this field of technology (EP-A 0 732 362; L. Panzer, American Chem. Soc., Rubber Div. Meeting 1997).

The preparation of organosilicon-disulfanes of high purity is difficult for the expert, because known processes, such as, for example, the reaction of 3-chloropropyltriethoxysilane with $Na_2S_2$, lead to product mixtures with contents of monosulfane or long-chain oligosulfanes. These contents are undesirable, however, because monosulfane is inactive in the application, and the long-chain oligosulfanes lead to undesirable effects in the mixing processes.

It is known to prepare organosilicon-disulfanes of high purity by disulfurizing polysulfanes with cyanides, phosphanes or sulfites (EP-A 0 773 224).

This process has the disadvantage that a polysulfane must first be prepared, which is then degraded to the disulfane. Another disadvantage is the use of toxic substances such as cyanides and such as phosphanes.

It is furthermore known to prepare organosilicon-disulfanes by oxidizing the corresponding mercaptosilanes by means of $MnO_2$ or $SO_2Cl_2$ (EP-A 0 718 392; DE-A 23 60 470).

The known processes have the disadvantage that a mercaptosilane is employed as an educt, which must be prepared by an industrially involved process from the corresponding chloroalkylsilanes and thiourea, with subsequent cleavage of the thiruronium salt.

It is therefore an object of the present invention to avoid the disadvantages and shortcomings of the prior known technology.

SUMMARY OF THE INVENTION

The above and other objects of the present invention can be achieved by a process for the preparation of organosilicon-disulfanes, which is characterized in that organo silicon thiocyanates are decomposed in the presence of alkali metal alcoholates, either in situ or after their isolation.

DETAILED DESCRIPTION OF INVENTION

In one embodiment of the invention, the organosilicon-disulfanes can correspond to the general formula $$Z\text{-Alk-}S_2\text{-Alk-}Z \qquad (I)$$

in which Z represents, a member selected from the group consisting of

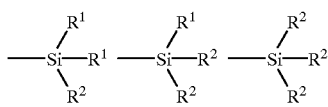

in which $R^1$ represents a linear or branched alkyl group having 1–5 C atoms, cycloalkyl having 5–8 C atoms, benzyl, or phenyl optionally substituted by methyl, ethyl or chlorine, $R^2$ represents an alkoxy group with a linear or branched carbon chain having 1–5 C atoms, or represents a cycloalkoxy group having 5–8 C atoms, the phenoxy group or the benzyloxy group, where $R^1$ and $R^2$ can in each case have identical or different meanings, Alk represents a divalent saturated linear or branched hydrocarbon radical having 1–10 C—atoms or the group

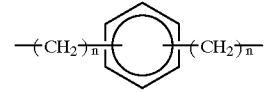

wherein n can be =1 to 6.

Thiocyanates which can be employed are compounds of the formula $$Z\text{-Alk-SCN} \qquad (II)$$

in which Z and Alk have the abovementioned meanings.

As the alkali metal alcoholate there may be employed compounds of the formula $$R^3O\text{—Me} \qquad (III)$$

in which $R^3O$ represents an alkoxy group with a linear or branched carbon chain and 1 to 5 C atoms, or represents a cycloalkoxy group having 5 to 8 C atoms, the phenoxy group or the benzyloxy group and Me is sodium or potassium.

Preferably, the alkoxy groups $R^3O$ of the alcoholate can correspond to the alkoxy radical $R^1$ of the organosilicon thiocyanate.

In a preferred embodiment of the invention, the thiocyanates employed according to the invention can be used not as the isolated and purified end product, but can be employed as the crude product in a one-pot reaction, without isolation, in the synthesis, which is known per se, from halogenorganosilicon compounds of the formula $$Z\text{-Alk-Hal} \qquad (IV)$$

in which Z and Alk have the abovementioned meanings and Hal represents a chlorine, bromine or iodine atom, and alkali metal thiocyanates of the formula:

$$Me\text{—SCN} \qquad (V)$$

wherein Me represents Na, K or ammonium.

The reaction of the organosilicon thiocyanates with alkali metal alcoholates can take place in an organic solvent.

Organic solvents which can be employed are in principle all polar substances which do not react with the organosilicon compound according to formula II.

A linear or branched alcohol having 1–5 C atoms, such as, for example, methyl, ethyl, propyl, butyl or pentyl alcohol, can preferably be used as the organic solvent. Cycloalkyl alcohols having 5–8 C atoms, phenol or benzyl alcohol are also suitable.

The reaction can be carried out both under atmospheric pressure conditions and under increased or reduced pressure. The temperature necessary for the reaction is between ambient temperature and the boiling temperature of the particular solvent which is established under the pressure conditions used. Preferably, the reaction is carried out at temperatures close to the boiling point of the solvent used, in order to achieve short reaction times.

A highly pure disulfane, the purity of which is significantly above the value required according to EP-A 0 732 362 for use in rubber reinforced with silica of at least 80% and which, without a further purification step, is also significantly superior in respect of disulfide content to the products

EXAMPLE 1

Preparation of bis(3,3'-triethoxysilylpropyl)disulfane from 3-thiocyanatopropyltriethoxysilane 2.3 g (0.10 mol) elemental sodium are dissolved in 100 ml ethanol under nitrogen in a glass apparatus with a 500 ml three-necked flask, dropping funnel and reflux condenser. After all the sodium has reacted to give sodium ethylate, the mixture is heated to the boiling temperature, and when reflux is reached, 52.7 g (0.20 mol) 3-thiocyanatopropyltriethoxysilane are added dropwise in the course of 30 min. When the addition has ended, the mixture is allowed to react under reflux for a further three hours. After cooling to room temperature, the yellowish solution, which contains a colourless precipitate, is evaporated at 80° C. in vacuo (final vacuum 40 mbar). The colourless precipitate is filtered off. 39.6 g (0.08 mol) bis(3,3'-triethoxysilylpropyl)disulfane are obtained (yield 83%). The identity of the product is confirmed by a $^1$H-NMR spectrum.

EXAMPLE 2

Preparation of bis(3,3'-triethoxysilylpropyl)disulfane from 3-chloropropyltriethoxysilane, sodium thiocyanate and sodium methanolate 48.16 g (0.20 mol) 3-chloropropyltriethoxysilane are heated at 1200C together with 18.65 g (0.23 mol) sodium thiocyanate in 100 ml ethanol for 10 h in an autoclave. After cooling, the crude product obtained is added dropwise, in the apparatus of example 1, to a boiling sodium alcoholate solution prepared from 2.3 g (0.10 mol) elemental sodium and 50 ml ethanol. When the addition is complete, the mixture is further heated under reflux for another 3 h, cooled and then filtered. The filter-cake is washed twice with 30 ml ethanol each time and the combined filtrates are then evaporated at 800C in vacuo (final vacuum 40 mbar). After renewed filtration of the evaporation residue, 37.8 g (0.08 mol) bis(3,3'-triethoxysilylpropyl) disulfane are obtained (yield based on 3-chloropropyltriethoxysilane 80%). The identity and purity of the product is confirmed by a $^1$H-NMR spectrum.

Further variations and modifications of the foregoing will be apparent to those skilled in the art and are intended to be encompassed by the claims appended hereto.

German priority application 198 48 482.8 filed Oct. 21, 1998 is relied on and incorporated herein by reference.

We claim:

1. A process for the preparation of an organosilicon-disulfane, comprising decomposing an organosilicon thiocyanate in the presence of alkali metal alcoholate, either in situ or after isolation.

2. A process for the preparation of an organosilicon-disulfane corresponding to the formula:

$$Z\text{-Alk-}S_2\text{-Alk-}Z \qquad (I)$$

in which Z represents, a member selected from the group consisting of $$-\underset{R^2}{\overset{R^1}{\underset{|}{\text{Si}}}}-R^1 \quad -\underset{R^2}{\overset{R^1}{\underset{|}{\text{Si}}}}-R^2 \quad -\underset{R^2}{\overset{R^2}{\underset{|}{\text{Si}}}}-R^2$$

in which $R^1$ represents a linear or branched alkyl group having 1–5 C atoms, cycloalkyl having 5–8 C atoms, benzyl, or phenyl optionally substituted by methyl, ethyl or chlorine, $R^2$ represents an alkoxy group with a linear or branched carbon chain having 1–5 C atoms, or represents a cycloalkoxy group having 5–8 C atoms, the phenoxy group or the benzyloxy group, where $R^1$ and $R^2$ can in each case have identical or different meanings, Alk represents a divalent saturated linear or branched hydrocarbon radical having 1–10 C—atoms or the group $$-(CH_2)_n-\underset{}{\bigcirc}-(CH_2)_n-$$

wherein n can be =1 to 6 comprising reacting a thiocyanate of the formula:

$$Z\text{-Alk-SCN} \qquad (II),$$

in which Z and Alk have the abovementioned meanings in the presence of an alkali metal alcoholate of the formula:

$$R^3O-Me \qquad (III),$$

in which $R^3O$ represents an alkoxy group with a linear or branched carbon chain and 1 to 5 C atoms, or represents a cycloalkoxy group having 5 to 8 C atoms, the phenoxy group or the benzyloxy group and Me is sodium or potassium.

3. The process according to claim 2 wherein the thiocyanate is the crude product obtained in a one-pot reaction, without isolation, from a halogenorganosilicon compound of the formula $$Z\text{-Alk-Hal} \qquad (IV)$$

in which Z and Alk have the abovementioned meanings and Hal represents a chlorine, bromine or iodine atom, and an alkali metal thiocyanate $$Me-SCN \qquad (V)$$

wherein Me represents Na, K or ammonium.

4. The process according to claim 2 further comprising reacting in the presence of an organic solvent.

5. The process according to claim 4 further comprising heating to the boiling point of the organic solvent.

6. The process according to claim 2 wherein a halogenorganosilane is heated with an alkali metal thiocyanate in the presence of an organic solvent to obtain a crude product, then the crude product is added to a boiling alkali metal alcoholate solution, thereafter the resulting mixture is heated under reflux to obtain the desired product.

7. The process according to claim 2 wherein 3-thiocyanateo propyltriethoxy silane is added to a boiling solution of sodium ethylate and the resulting mixture is refluxed for a sufficient period of time to produce the desired product, and precipitating the product.

* * * * *